United States Patent
Nakamura et al.

(10) Patent No.: US 7,422,326 B2
(45) Date of Patent: Sep. 9, 2008

(54) MONKEY VISUAL FIELD MEASUREMENT SYSTEM AND VISUAL FIELD MEASUREMENT METHOD

(75) Inventors: Katsuki Nakamura, Kodaira (JP); Masaaki Sasaoka, Ikoma (JP)

(73) Assignee: Santen Pharmaeutical Co., Ltd., Osaka (JP)

( * ) Notice: Subject to any disclaimer, the term of this patent is extended or adjusted under 35 U.S.C. 154(b) by 455 days.

(21) Appl. No.: 10/483,318

(22) PCT Filed: Jul. 3, 2002

(86) PCT No.: PCT/JP02/06761

§ 371 (c)(1),
(2), (4) Date: Sep. 10, 2004

(87) PCT Pub. No.: WO03/007807

PCT Pub. Date: Jan. 30, 2003

(65) Prior Publication Data

US 2006/0232742 A1    Oct. 19, 2006

(30) Foreign Application Priority Data

Jul. 10, 2001    (JP)    ............................. 2001-209273

(51) Int. Cl.
*A61B 3/14*    (2006.01)

(52) U.S. Cl. ..................................... 351/206; 351/209
(58) Field of Classification Search ................. 359/206, 359/209; 351/206, 209
See application file for complete search history.

(56) References Cited

U.S. PATENT DOCUMENTS

| 5,668,622 | A  | * | 9/1997 | Charbonnier et al. | ........ 351/209 |
| 6,260,970 | B1 | * | 7/2001 | Horn               | ........ 351/246 |
| 6,373,961 | B1 | * | 4/2002 | Richardson et al.  | ........ 382/103 |

FOREIGN PATENT DOCUMENTS

JP    58-121937 A    7/1983

(Continued)

*Primary Examiner*—Jordan M. Schwartz
*Assistant Examiner*—James C Jones
(74) *Attorney, Agent, or Firm*—The Webb Law Firm

(57) ABSTRACT

The present invention relates to a system and a method for determining a field of a vision of a monkey. Its object is to provide a system and a method which can cause a monkey to effect accurate visual field determination like a human subject. To achieve the object, according to the invention, there is provided a system for determining visual field of a monkey, comprising: a head fixing unit (A) for fixing a chair (1) to be seated by the monkey and the monkey's head; an eye target display unit (B) for displaying a gazing point (2) at which the monkey is caused to fix its eye and displaying also an eye target (3) at a predetermined position within the monkey's visual field with a predetermined brightness; a gazing monitor unit (C) for monitoring the direction of the monkey's gazing; and a response lever (4) by which the monkey shows that it has recognized the eye target; wherein the head fixing unit (A) includes an attachment member (5) fixable to the top of the monkey's head, a support member (6) connectable to the attachment member (5), and a base member (7) for fixing the support member (6). There is also provided a method for determining a visual field of a monkey using this system.

9 Claims, 2 Drawing Sheets

FOREIGN PATENT DOCUMENTS

| | | |
|---|---|---|
| JP | 59-218137 A | 12/1984 |
| JP | 2-136124 A | 5/1990 |
| JP | 3-2584 A | 1/1991 |
| JP | 7-147862 A | 6/1995 |
| JP | 8-150129 A | 6/1996 |
| JP | 10-500340 A | 1/1998 |
| JP | 10-99279 A | 4/1998 |
| JP | 11-27653 A | 1/1999 |
| WO | WO 99/63889 A1 | 12/1999 |

* cited by examiner

MONKEY VISUAL FIELD MEASUREMENT SYSTEM AND VISUAL FIELD MEASUREMENT METHOD

TECHNICAL FIELD

The present invention relates to a system and a method for determining field of vision of a monkey.

BACKGROUND ART

Glaucoma, a disease generally caused by rise in blood pressure in the eye, gives damage to the visual nerve system, leading to a symptom of loss of vision. Various medical products have been developed and put into use as therapeutical agents for this glaucoma. In research and development of medical products in general, not limited to those of the therapeutical agents for glaucoma, an efficacy test of the agent using animals as subjects is essential before it is put for use in a clinical test. Since glaucoma is a disease leading to loss of vision as described above, it is preferred that such efficacy test be effected in the form of determination of visual field. However, it is extremely difficult to conduct determination of visual field with high accuracy with using an animal subject. Therefore, in actuality, the efficacy test has been conducted not in the form of determination of visual field, but in the form of determination of ophathalmotonometry (eye blood pressure).

On the other hand, as an instrument for determining visual field, a Humphrey field analyzer is usually employed. This field analyzer was developed for determining visual field of human. In its use, a subject is seated in front of an eye target display screen and instructed to fix his/her eye on a gazing point illuminated at a substantially center position in the eye target display screen. Under this condition, an eye target is illuminated at a predetermined position in the eye target display screen, and when the subject recognizes this illumination, the subject shows it by e.g. pressing a response button. During this determination, the subject assumes a posture with his/her chin placed on a fixing platform for fixing the subject's head.

As described above, in the research and development of a therapeutic agent for glaucoma, the determination of visual field has an important roll. Hence, there has been a need to develop a technique which allows an efficacy test to be conducted by way of visual field determination using an animal subject. It is known that there exists close correlation of central cavity visual function between the human and the monkey. Then, if the determination of visual field with using a monkey is made possible, this will help deduce the efficacy of the agent in a human subject with higher accuracy, thus being very useful for the research and development of therapeutic agent for glaucoma.

However, the above-described Humphrey field analyzer was developed for determination of visual field of humans. So, although this instrument can be appropriately used when smooth communication is possible between the operator and the subject, it is difficult to use this for determination of visual field of a money with which communication is not easy.

Further, in the determination of visual field, it is determined to which level of illumination the subject can recognize each position in his/her field of vision. The greater the number of points determined and the greater the number of levels of brightness determined at the respective points, the higher the accuracy of the measurement result. However, in the case of the Humphrey field analyzer, considering the time period when a human subject can keep his/her concentration in the determination, the instrument is designed so that the determination is completed in a short period of time. Therefore, it is not possible to determine a threshold value with varying the brightness in small increments or to conform the reproducibility of the determined values. In this respect, the instrument is not satisfactory in terms of the accuracy of the visual field determination.

For this reason, there has been a need for developing a system and a method which allow accurate determination of visual field of a monkey. In addition, since the Humphrey field analyzer is expensive, there has also been a need for a less costly determining system utilizing a general-purpose instrument.

An object of the present invention is to provide a system and a method for determining visual field of a monkey, which allow high accuracy determination of visual field of a monkey just like that of a human subject.

DISCLOSURE OF THE INVENTION

A system for determining visual field of a monkey, according to the present invention, comprises: a head fixing unit for fixing a chair to be seated by the monkey and the monkey's head; an eye target display unit for displaying a gazing point at which the monkey is caused to fix its eye and displaying also an eye target at a predetermined position within the monkey's visual field with a predetermined brightness; a gazing monitor unit for monitoring the direction of the monkey's gazing; a calculating unit for analyzing data; and a response lever by which the monkey shows that it has recognized the eye target; wherein the head fixing unit includes an attachment member fixable to the top of the monkey's head, a support member connectable to the attachment member, and a base member for fixing the support member.

With the above-described construction, the attachment member constituting the head fixing unit is attached to the top of the monkey's head. This eliminates need to apply an external force such as a fastening force, to fix the monkey's head in position. As a result, no stress is given to the monkey and the visual field determination can proceed with the monkey being under a relaxed state.

Further, when the monkey is fixed by the top of its head, it is possible to expect the following effect.

Normally, when the monkey moves its head without moving its entire body, this head movement usually occurs in the form of swinging of the head about the neck to the right and left. Therefore, by fixing the top portion of the head which portion is the most distant portion of the head from the neck, it is possible to resist such head movement of the monkey with the minimum possible force. As a result, the fixing of the monkey's neck requires only a small force. This is believed to decrease the stress given to the monkey.

In addition to the above, the invention's system for determining visual field of a monkey comprises the support member connectable to the attachment member and the base member for fixing the support member. Then, if these members are provided separately from the attachment member, for fixing the attachment member to the top of the monkey's head, this requires only surgical attachment of this small attachment member thereto prior to the determination. Therefore, until the fixation of the monkey's head to the base member is completed, it is possible to reduce the feeling of discomfort to the monkey. Accordingly, the visual field determination can proceed with the monkey being much relaxed, so the visual filed determination result with high reliability can be obtained.

With the invention's system for determining visual field of a monkey, the head fixing unit can be configured to be out of the monkey's visual field. With this arrangement of keeping the head fixing unit out of the monkey's visual field, it becomes possible not to restrict the monkey's visual field, thereby to avoid interference with the visual field determination. Further, another effect can be expected, i.e. effective prevention of loss of calmness of the monkey when it views the head fixing unit.

With the invention's system for determining visual field of a monkey, the support member can be adapted to be speedily connectable with the attachment member and adapted also to be length-adjustable. With the possibility of speedy connection between the support member and the attachment member, it is possible to reduce the set-up time for the visual field determination. As a result, the visual field determination can be started with keeping minimum the stress which may be given to the monkey during the time of set-up until the time of the visual filed determination. Further, the length adjustability of the support member can accommodate size difference if any in the monkey's head. As a result, the head can be adjusted in position so that it may be set to provide an appropriate eyeball position.

With the invention's system for determining visual field of a monkey, the gazing monitor unit includes an infrared LED array for irradiating infrared beam to the pupil of the monkey's eye, and a CCD camera and the shape of the monkey's pupil imaged by the CCD camera is approximated to an oval with the center of the oval representing the center of the pupil, and a comparison calculation is made between the gazing point and the position coordinates of the pupil obtained in advance by causing the monkey to fix its eye on a desired position adjacent the gazing point, thereby to continuously determine the direction of the monkey's gazing in realtime. This construction provides the following advantage.

Namely, as a gazing monitor unit employed in the conventional ophthalmological instrument, there is known e.g. a unit adapted for projecting infrared beam to the cornea of the subject's eye and then electrically detecting any displacement of the infrared beam reflected by the surface of cornea. However, such instrument requires a device for projecting the infrared beam and it is also necessary to arrange such device in alignment with the gazing. Hence, the instrument tends to be complicated.

In this regard, according to the system of the invention which simply irradiates the infrared beam to the cornea and effects image processing of the movement of the cornea captured by the CCD camera, the above-described drawbacks of the conventional system are overcome and the gazing monitor device can be simple and convenient. Especially, in the case of the construction of the present invention, there is no need to arrange the component such as the CCD camera or the like on the gazing, so that there will occur no interference with the visual field determination. Moreover, by continuously determining the direction of the monkey's gazing in realtime, the visual field determination result can instantly reflect the gazing data.

With the invention's system for determining visual field of a monkey, the system can further employ a general-purpose personal computer in data analysis. With this possibility of analysis using a general-purpose personal computer, it is possible to provide a less costly determining system, as compared with the conventional Humphrey field analyzer.

On the other hand, the invention's method for fixing a head of a test subject animal is characterized in that after an attachment member is fixedly attached to a top of the head of a monkey, a portion of a support member is connected to this attachment member and then the support member is fixed to a base member.

With this method, as described hereinbefore regarding the function/effect of the visual field determining system, no external force such as a fastening force is applied when the monkey's head is to be fixed. Therefore, no stress is given to the monkey and the visual field determination can be effected while the monkey is relaxed.

Further, since the attachment member and the support member can be connected speedily to each other, the set-up time prior to the visual field determination can be shortened, so that the visual field determination can then proceed smoothly, without giving stress to the monkey.

Also, as the top of the monkey's head is fixed, only small force is needed for fixing the monkey's neck, so that the stress given to the monkey can be further reduced.

Further, with the above-described characterizing means, the member attachable to the monkey's head, i.e. the attachment member which is small as a whole, may be surgically attached to the top of the monkey's head in advance. For this reason, it is possible to reduce the discomfort to the monkey not only in the daily life of the monkey, but also when the monkey's head is completely fixed to the base member. Accordingly, the visual field determination can be carried out with the monkey being under a more relaxed condition. Hence, visual field determination result with higher reliability can be obtained.

On the other hand, according to the invention's method of determining a field of a vision of a monkey comprises the steps of: seating the monkey at a chair with an attachment member being fixed to the top of the monkey's head; connecting a portion of a support member to the attachment member; fixing the support member to a base member; and then illuminating a gazing point in an eye target display screen placed in front of the monkey in response to the monkey's pressing a response lever; illuminating an eye target at a predetermined position in the monkey's visual field with predetermined brightness while the monkey is gazing at the gazing point and pressing the response lever; and releasing the pressing of the response lever when the eye target is illuminated.

In case the top of the monkey's head is fixed, the stress given to the monkey can be reduced, so it can be expected to obtain measurement data with high reliability, as described hereinbefore.

Further, by fixing the head, it is possible to avoid gazing failure due to a movement of the monkey's head. As a result, the monkey can easily gaze at the gazing point and the stress to the monkey can be reduced, whereby measurement data with good reproducibility can be obtained.

Also, with this method which releases the pressing of the response lever when the monkey shows that it has recognized the eye target, it is possible to reduce the response time. That is, the response lever is constructed as a spring-urged mechanism. Hence, a positive pressing force needs to be applied against the spring urging force when the response lever is to be depressed. On the other hand, releasing the response lever requires only the monkey's releasing the pressing force, whereby the response lever is automatically returned by the spring urging force. Accordingly, the initiation of the activation of the response lever can be very much quickened, so an accurate response can be made.

As described above, using the determining system which can reduce the stress to the monkey and which is easy to operate and which provides an accurate response, visual field determination result with even higher reliability can be obtained.

With the invention's method of determining a visual field of a monkey, in addition to the above, for confirming whether the monkey is gazing at the gazing point or not, an infrared LED array is used for irradiating infrared beam to the pupil of the monkey's eye, and a CCD camera is used for monitoring the monkey's pupil, the shape of the monkey's pupil being approximated to an oval, with the center of the oval representing the center of the pupil, and a comparison calculation is made between the gazing point and the position coordinates of the pupil obtained in advance by causing the monkey to gaze at a desired position adjacent the gazing point, thereby to continuously determine the direction of the monkey's gazing in realtime.

With this characterizing means, as described hereinbefore regarding the function/effect of the visual field determining system, the method employs a convenient gazing monitor device and this device can be disposed at a position not interfering with the visual field determination. Hence, while the method is economical, it is yet possible to obtain visual field determination result which instantly the gazing data having high reliability.

Further, by using the visual field determining system described above, it is also possible to provide an efficacy determining method for therapeutic agent for glaucoma.

By using the present system, visual field determination of a monkey can be effected with accuracy, and progression condition or the like of loss of visual field can be grasped in details. For this reason, in research and develop of a new drug for use in treatment of glaucoma, it is possible to obtain sufficient experiment data for confirming efficacy of the new drug, prior to its use in a clinical test.

Figure 1:
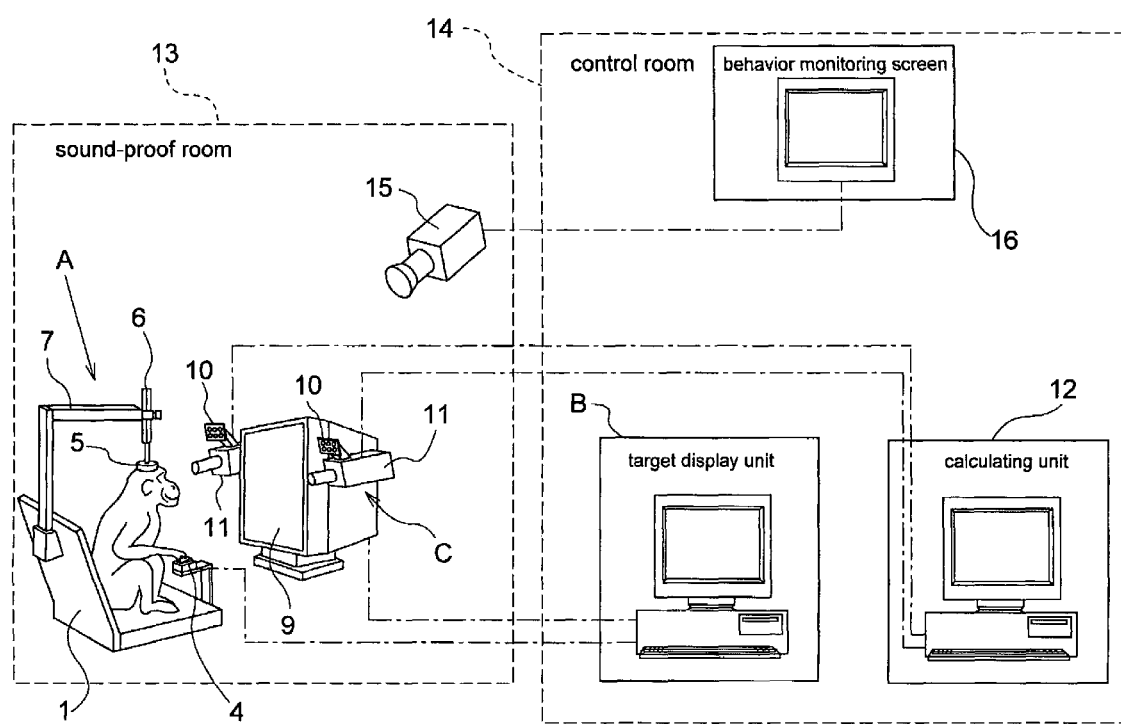
FIG. 1 is an explanatory view showing a construction of a system for determining a field of a vision of a monkey relating to the present invention.

BEST MODE OF EMBODYING THE INVENTION (Summary)

The visual field determining system and method relating to the present invention are designed for a monkey as the subject. As described hereinbefore, if determination of a visual field of a monkey is made possible, this will be very useful for research and development of a therapeutic agent for glaucoma.

The invention's system for determining a visual field of a monkey includes the following major components.

First, the system includes a head fixing unit A for fixing a chair 1 to be seated by a monkey and the monkey's head. For obtaining visual field determination result with high reliability, it is essential to fix the monkey's head.

Next, the system includes an eye target display unit B, a gazing monitor unit C and a calculating unit 12. The eye target display unit B displays a gazing point 2 at which the monkey is caused to gaze and displays also an eye target 3 at a predetermined position within the visual field of the monkey with a predetermined brightness. The gazing monitor unit C monitors the direction of the gazing of the monkey. This is because for visual field determination the gazing point 2 as a stationary point needs to be looked at constantly.

The system further includes a response lever 4 by which the monkey shows that it has recognized the eye target 3. This response lever 4 is normally operated by a hand.

Next, the visual field determining system and the visual field determining method relating to the present invention will be described with reference to the accompanying drawings.

(Fixation of Head)

Figure 2:
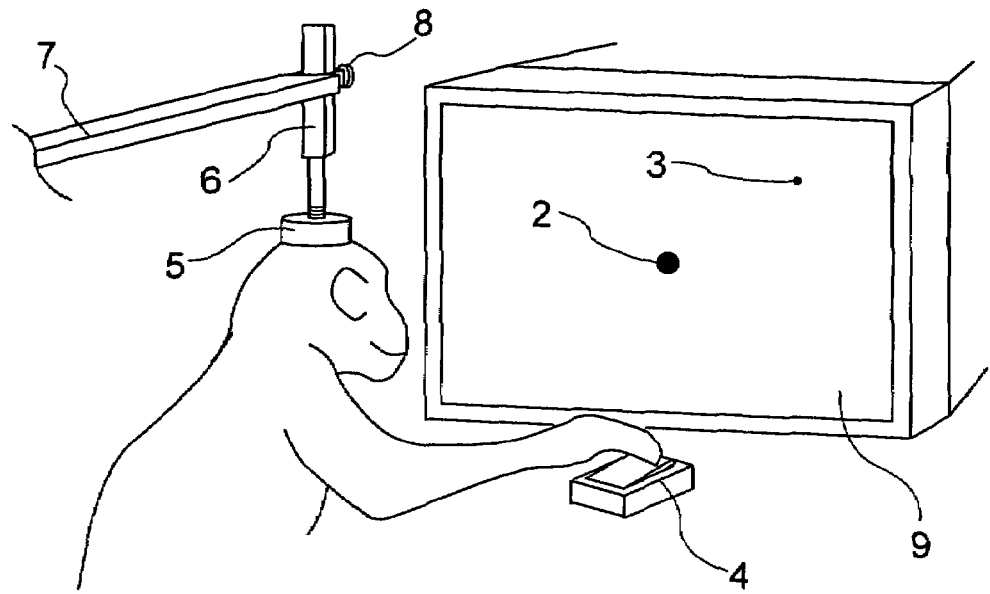
FIG. 2 is an explanatory view showing a procedure for fixing a monkey's head.

According to the invention's method, as shown in FIG. 1 and FIG. 2, the top of the monkey's head is fixed.

In order to fix an attachment member 5 to the top of the monkey's head in advance, the monkey is subjected to a surgical operation, in which first the monkey's skull is exposed by incision of the skin of the head top and then into this exposed skull a screw made of a material such as stainless steel, silicone or the like not inviting inflammation is driven and thereafter to this screw the attachment member 5 is fixedly attached. In this embodiment, as this attachment member 5, there is employed a resin cement for dental treatment in which e.g. a cylindrical stainless steel element is embedded. The bonding among the screw, the skull and the attachment member 5 utilizes polymerization of the resin. After the surgical operation, the operated portion is left until curing of the resin cement is completed. The fixation of the head requires only inserting the bar-like support member 6 into the cylindrical stainless steel portion and fixedly threading thereto.

When determination of the visual field is to be effected, the support member 6 is attached to the attachment member 5 and further the support member 6 is fixed to the base member 7. This base member 7 is formed integrally with the seat 1 to be seated by a monkey. For attachment of the support member 6 with the base member 7, e.g. a main portion of the bar-like support member 6 is inserted into an insertion hole formed in the base member 7. And, the support member 6 can be fixed by using a screw 8 or a clamp of various types or the like. With this construction, the height of the chair 1 seated by a monkey is adjustable in accordance with a seated height of the monkey, so that the monkey can assume a relaxed posture.

Further, with the support member 6 which is length adjustable, a difference in the size of the monkey's head can be adjusted. As a result, the position of the head can be adjusted so as to obtain an appropriate eye ball position.

In this way, with the construction of fixing the top of the head by using the attachment member 5 and so on, no fastening force is applied to the monkey's head. Thus, the stress given to the monkey can be alleviated.

Further, in the case of this construction fixing the head top, it is possible to adapt the head fixing unit A to be out of the monkey's visual field.

Moreover, in the case of the construction fixing the head top, the following effect can also be achieved. When the head is moved without being accompanied by a movement of the entire body, this usually takes the form of swinging movement of the head about the neck to the right and left. Therefore, if the top portion of the head which portion is most distant from the neck is fixed, it is possible to resist, with a minimum force, the force of the monkey which tries to move its head. As a result, only a small force is needed for fixing the monkey's neck, so that the components such as the attachment member 5 may be formed compact. Accordingly, it is possible to minimize the discomfort felt by the monkey, such as the discomfort of a foreign object being attached hereto and the stress given to the monkey can be further reduced.

Incidentally, in this embodiment, the attachment member 5 is comprised of the resin cement for dental treatment. However, the invention is not limited thereto. Alternatively, this member may be comprised, for example, of other type of rein having biocompatibility.

Further, by fixing the head, it is possible to avoid gazing failure due to a movement of the monkey's head. As a result, it becomes also possible for the monkey to easily gaze at the gazing point. Hence, with reduction of the stress to the monkey, measurement data with good reproducibility can be obtained.

(Fixing and Monitoring of Monkey's Gazing)

In order to fix the monkey's gazing, like the case of visual field determination of a human, a small white gazing point 2 is illuminated at a substantially center position in an eye target display screen 9. The illumination of the gazing point 2 and illumination of an eye target 3 to be described later are controlled by using a personal computer.

Regarding the illumination of the gazing point 2, for obtaining visual field determination data, the gazing point 2 is illuminated at a position substantially in front of an eye to be measured.

During the visual field determination, the gazing of the monkey is monitored by using e.g. the infrared LED array 10, the CCD camera 11, the calculating unit 12 for analyzing e.g. data of gazing position, etc.

Specifically, while infrared beam is irradiated to the monkey's eye by using the infrared LED array 10, the pupil of the monkey is monitored by the CCD camera 11. And, the shape of the pupil is approximated to an oval based on the shading distribution of this monitor image, thereby to obtain the center of this oval as the center of the pupil.

These components, i.e. the CCD camera 11 and infrared LED array 10 are prepared in two sets, so as to monitor the right and left eyes respectively. The two sets are provided for monitoring of the right and left eyes independently of each other.

The determination of the gazing direction is carried out as follows. In the eye target display screen 9, total of nine gazing points 2 can be illuminated for the purpose of calibration. Then, the monkey is caused to gaze at each point in advance, thereby to obtain coordinates data of the nine gazing points 2 on the eye target display screen 9 and data of each pupil position obtained by the CCD camera 11 in correlation with each other. In an actual determination, based on these data, the position of the pupil in the monitor image is converted into coordinate points on the eye target display screen 9 so as to confirm the direction of the gazing.

(Procedure of Visual Field Determination)

In order to sustain the monkey's concentration and also to keep constant luminosity of the ambience for improvement of accuracy of the visual field determination, the visual field determination is carried out inside a sound-proof chamber 13. Various control instruments used in the visual field determination are disposed in a control room 14 separated from the sound-proof chamber 13. The condition and appearance of the monkey are monitored by a behavior monitoring camera 15 and a behavior monitoring screen 16.

The interval between the start of the monkey's gazing at the gazing point 2 and the illumination of the eye target 3 is varied appropriately, so as to prevent the monkey from memorizing the illuminating timing of the eye target 3 and also to effectively sustain the monkey's concentration.

The eye target 3 is illuminated in a random manner at each position in the visual field and with appropriate variation of its brightness. With this, it is possible to know the limit of visual recognition at each area in the visual field.

The response lever 4 employed in the present embodiment is spring-urged so that the lever may be returned upon release of the lever by the monkey. The monkey has been trained so that it shows its visual recognition of the illumination of the eye target 3 by means of releasing the response lever 4.

With this method of releasing the pressing of the response lever 4, it is possible to reduce the response time. That is, the response lever 4 is the spring-biased mechanism. And, for depressing this response lever 4, a positive pressing force needs to be applied thereto against the urging force of the spring. On the other hand, when releasing the response lever 4, the response lever 4 can be immediately returned by the spring urging force simply by the monkey's releasing its pressing force. Therefore, the timing of initiation of the activation of the response lever 4 can be very quick, so an accurate response can be obtained.

The reliability of a monkey's response can be judged by checking the following respects.

(1) whether the monkey's gazing was directed at the gazing point 2 or not;

(2) whether the response time for the presentation of the eye target 3 is appropriate or not; and (3) whether an eye target 3 to which the monkey failed to respond was an eye target 3 that should have been recognized by the monkey or not.

Based on these judgment items, the eye target display control unit B effects the judgment for each presentation of the eye target 3. When the response is judged as reliable, a reward such as juice will be given to the monkey and at the same time a buzzer is sounded. The reward and the sounding of the buzzer are positive feedback for the monkey's response, which is believed to improve the monkey's motivation for the visual field determination.

(Example)

For fixing a monkey's head, resin cement for dental treatment in which a cylindrical stainless steel member was embedded was employed. As this resin cement, a resin cement which can resist deterioration after lapse of long time period will be appropriate in order to prevent easy inadvertent detachment of the attachment member from the monkey's head.

For the visual field determination, first, the monkey is caused to gaze at the gazing point 2 illuminated in front of the monkey. While this gazing point 2 is being gazed at, the eye target 3 is illuminated at a predetermined position within the visual field. During the determination, movements of the monkey's eyeball are constantly monitored by the method described above.

The eye target 3 can be varied in its brightness by increment/decrement of 1 dB. The unit "dB" used here is a unit which is commonly employed by many field analyzers as the unit of brightness. The unit "dB" represents relative brightness and the maximum brightness of the field analyzer is 0 dB. The brightness setting in this embodiment was done in accordance with the Humphrey field analyzer. 0 dB corresponds substantially to the brightness of sunshine. As the relative brightness is varied from this to 1 dB 2 dB . . . , the brightness is reduced each time by 0.8 time approximately.

If the monkey provides reliable response such as response by releasing the response lever 4 disposed near its hand within a predetermined period following the illumination of the eye target 3 with a certain brightness, a reward is given to the monkey.

Figure 3:
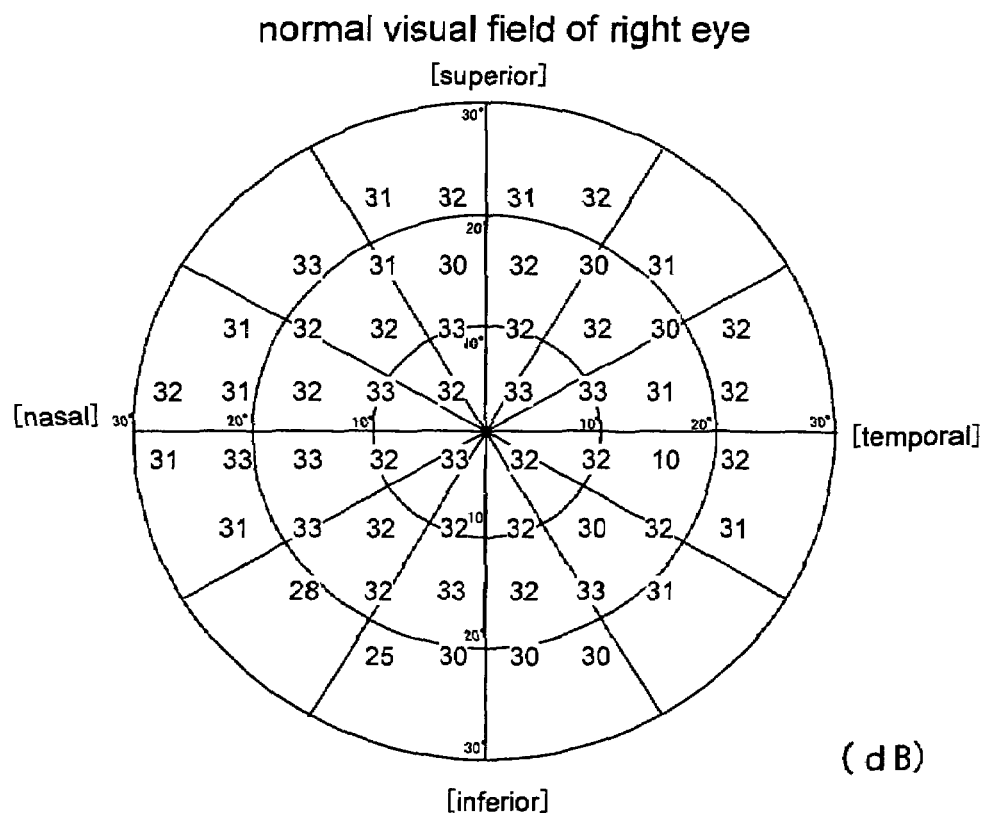
FIG. 3 is an explanatory view showing result of visual field determination of a monkey.

FIG. 3 shows the result of determination carried out by the manners described above.

This data comprise visual field data of a right eye of a crab-eating monkey (11 years old male). The eye target presenting positions in this data were in accordance with the Humphrey Central 24-2 in clinical use.

The brightness of the eye target 3 at each determination point was varied stepwise by 1 dB. In doing this, there was employed a method (adaptive strategy) for varying the strength of presenting stimulation in accordance with a response from the monkey. The above-described visual filed data were arranged in order based on the determination result by using an average value of brightness of the eye target 3 at each determination point at the timing of arrival at a threshold value which is believed to indicate visual recognition, that is, equilibrium.

(Effect)

It has been shown that the use of the invention's system and method for determining a field of vision of a monkey permits accurate visual field determination of the monkey.

And, by effecting a visual field determination of a monkey by using the present system, in e.g. development of a new drug for use in treatment of glaucoma, it becomes possible to obtain experiment data for confirming e.g. efficacy of the new drug prior to its clinical test using a human.

Further, as the system can use a general-purpose instrument, the system can be inexpensive.

INDUSTRIAL APPLICABILITY

As described above, the invention's system and method for determining a field of a vision of a monkey are suitable for causing a monkey to effect an accurate visual field determination. And, causing a monkey to effect such accurate visual field determination is very useful for research and development of a therapeutic agent for glaucoma.

The invention claimed is:

1. A system for determining visual field of a monkey, comprising:
    a head fixing unit (A) for fixing a chair (1) to be seated by the monkey and the monkey's head;
    an eye target display unit (B) for displaying a gazing point (2) at which the monkey is caused to fix its eye and displaying also an eye target (3) at a predetermined position within the monkey's visual field with a predetermined brightness;
    a gazing monitor unit (C) for monitoring the direction of the monkey's gazing;
    a calculating unit (12) for analyzing data; and
    a response lever (4) by which the monkey shows that it has recognized the eye target;
    wherein the head fixing unit (A) includes an attachment member (5) fixable to the top of the monkey's head, a support member (6) connectable to the attachment member, and a base member (7) for fixing the support member.

2. The visual field determining system for a monkey according to claim 1, wherein the head fixing unit (A) is configured to be out of the monkey's visual field.

3. The visual field determining system for a monkey according to claim 1, wherein the support member (6) is adapted to be speedily connectable with the attachment member (5) and adapted also to be length-adjustable.

4. A system for determining visual field of a monkey, comprising:
    a head fixing unit (A) for fixing a chair (1) to be seated by the monkey and the monkey's head;
    an eye target display unit (B) for displaying a gazing point (2) at which the monkey is caused to fix its eye and displaying also an eye target (3) at a predetermined position within the monkey's visual field with a predetermined brightness;
    a gazing monitor unit (C) for monitoring the direction of the monkey's gazing;
    a calculating unit (12) for analyzing data; and
    a response lever (4) by which the monkey shows that it has recognized the eye target;
    wherein the head fixing unit (A) includes an attachment member (5) fixable to the top of the monkey's head, a support member (6) connectable to the attachment member, and a base member (7) for fixing the support member;
    the gazing monitor unit (C) includes an infrared LED array (10) for irradiating infrared beam to the pupil of the monkey's eye, and a CCD camera (11);
    the shape of the monkey's pupil imaged by the CCD camera is approximated to an oval with the center of the oval representing the center of the pupil, and
    a comparison calculation is made between the gazing point and the position coordinates of the pupil obtained in advance by causing the monkey to fix its eye on a desired position adjacent to the gazing point, thereby to continuously determine the direction of the monkey's gazing in real-time.

5. The visual field determining system for a monkey according to claim 1, wherein said calculating unit (12) comprises a general-purpose personal computer.

6. A method of determining a field of a vision of a monkey comprising the steps of:
    seating the monkey in a chair (1) with an attachment member (5) being fixed to the top of the monkey's head;
    connecting a portion of a support member (6) to the attachment member;
    fixing the support member to a base member (7); and then illuminating a gazing point (2) in an eye target display screen placed in front of the monkey in response to the monkey's pressing a response lever (4); illuminating an eye target (3) at a predetermined position in the monkey's visual field with predetermined brightness while the monkey is gazing at the gazing point and pressing the response lever; and releasing the pressing of the response lever when the eye target is illuminated.

7. The method of determining a field of a vision of a monkey according to claim 6, wherein for confirming whether the monkey is gazing at the gazing point (2) or not, an infrared LED array (10) is used for irradiating infrared beam to the pupil of the monkey's eye, and
    a CCD camera (11) is used for monitoring the monkey's pupil, the shape of the monkey's pupil being approximated to an oval, with the center of the oval representing the center of the pupil, and a comparison calculation is made between the gazing point and the position coordinates of the pupil obtained in advance by causing the monkey to gaze at a desired position adjacent to the gazing point, thereby to continuously determine the direction of the monkey's gazing in real-time.

8. A method of determining efficacy of a therapeutic agent for glaucoma using the visual field determining system as defined in claim 1.

9. A method for fixing a head of a test subject animal, wherein after an attachment member (5) is surgically attached and fixed to the top of the head of the test subject animal to fix the head of the test subject animal and determine the direction of the gazing of the test subject animal, a support member (6) is connected at one end thereof to this attachment member and is fixed at the other end thereof to a base member (7).

* * * * *

UNITED STATES PATENT AND TRADEMARK OFFICE
CERTIFICATE OF CORRECTION

PATENT NO. : 7,422,326 B2 Page 1 of 1
APPLICATION NO. : 10/483318
DATED : September 9, 2008
INVENTOR(S) : Nakamura et al.

It is certified that error appears in the above-identified patent and that said Letters Patent is hereby corrected as shown below:

Title page, Item (73) Assignee: "Santen Pharmaeutical Co., Ltd." should read -- Santen Pharmaceutical Co., Ltd. --

Signed and Sealed this

Seventeenth Day of February, 2009

JOHN DOLL
*Acting Director of the United States Patent and Trademark Office*